United States Patent [19] [11] 4,092,415
Schmid et al. [45] May 30, 1978

[54] MICROORGANISM COMBATTING QUINOXALINE-DI-N-OXIDE CARBOXAMIDES

[75] Inventors: Wolfgang Schmid, Therwil; Walter Basler; Burckhardt, Urs, both of Basel, all of Switzerland

[73] Assignee: Ciba-Geigy Corporation, Ardsley, N.Y.

[21] Appl. No.: 758,973

[22] Filed: Jan. 13, 1977

[30] Foreign Application Priority Data

Jan. 20, 1976 Switzerland .......................... 634/76
Nov. 26, 1976 Switzerland ........................ 14920/76

[51] Int. Cl.² ............... C07D 241/52; C07D 31/495
[52] U.S. Cl. ........................... 424/250; 260/561 K; 544/355
[58] Field of Search .................. 260/250 Q; 424/250

[56] References Cited

U.S. PATENT DOCUMENTS 3,635,972  1/1972  Cronin ........................ 260/250 Q
3,660,391  5/1972  Ley et al. .................... 260/250 Q

FOREIGN PATENT DOCUMENTS 1,670,935  2/1971  Germany.
1,620,114  3/1970  Germany.
1,223,720  3/1971  United Kingdom.

Primary Examiner—Donald G. Daus
Assistant Examiner—Mark L. Berch
Attorney, Agent, or Firm—Harry Falber

[57] ABSTRACT

Novel quinoxaline-di-N-oxide derivatives of the formula

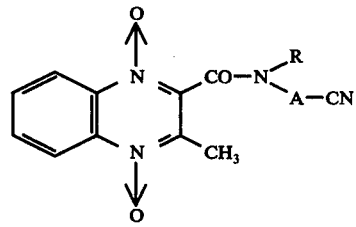

are disclosed, wherein
R represents a hydrogen atom, an alkyl group of 1 to 12 carbon atoms, a cyanoalkyl group containing 1 to 4 carbon atoms in the alkyl moiety or an allyl group, and
A represents a straight-chain or branched alkylene bridge member containing 1 to 4 carbon atoms.

These compounds are useful for the control of pathogenic microorganisms and for stimulating the growth of domestic animals and productive livestock.

12 Claims, No Drawings

MICROORGANISM COMBATTING QUINOXALINE-DI-N-OXIDE CARBOXAMIDES

The present invention relates to novel quinoxaline-di-N-oxide derivatives, a process for their manufacture, compositions which contain these derivatives as active component, a method of controlling pathogenic microorganisms which comprises the use of the novel compounds, and to the use thereof as feed additives for stimulating the growth of domestic animals and productive livestock.

The novel quinoxaline-di-N-oxide derivatives have the general formula I

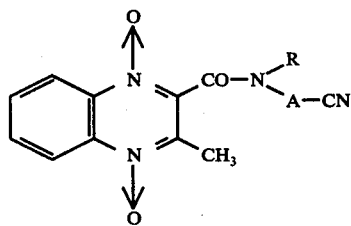

wherein
R represents a hydrogen atom, an alkyl group of 1 to 12 carbon atoms, a cyanoalkyl group containing 1 to 4 carbon atoms in the alkyl moiety or an allyl group, and
A represents a straight-chain or branched alkylene bridge member containing 1 to 4 carbon atoms.

By alkyl groups are meant the following groups: methyl, ethyl, the isomers of the propyl, butyl, pentyl, hexyl, heptyl, octyl, nonyl, decyl, undecyl and dodecyl group.

The compounds of the formula I can be obtained by methods which are known per se (cf. DOS No. 1,670,935).

The reaction can be illustrated by the following formulae:

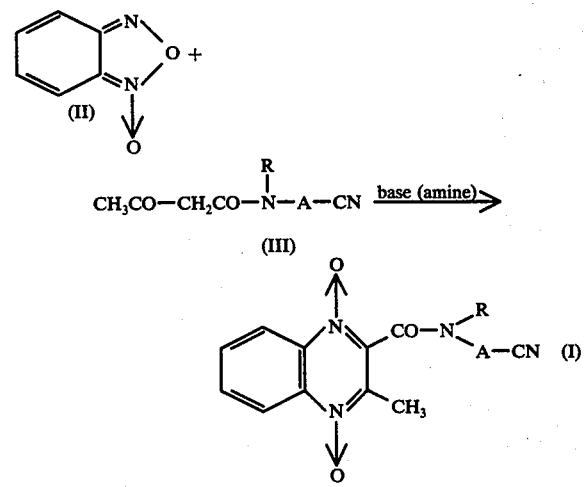

The reaction is carried out in an organic solvent which is inert to the reactants, such as an alcohol, acetonitrile, dimethyl formamide, tetrahydrofurane, dioxane, benzene, toluene or methyl cellosolve (ethylene glycol monomethyl ether), but preferably in methanol. It is advantageous if the reaction medium is as far as possible anhydrous.

The reaction is carried out at temperatures between 0° and 70° C, preferably between 30° and 50° C. The process is carried out in the presence of bases. Suitable bases are amines, preferably primary amines and ammonia.

A particularly advantageous embodiment of the synthesis of the compounds of the formula I comprises reacting the acetoacetic amide of the formula III (obtained in the preliminary step by reacting the aminonitrile with the diketene as starting material) in situ with the benzofuroxane of the formula II to give the desired compound of the formula I.

A further method of obtaining the compounds of the formula I is the following synthesis known from British patent specification No. 1,308,370:

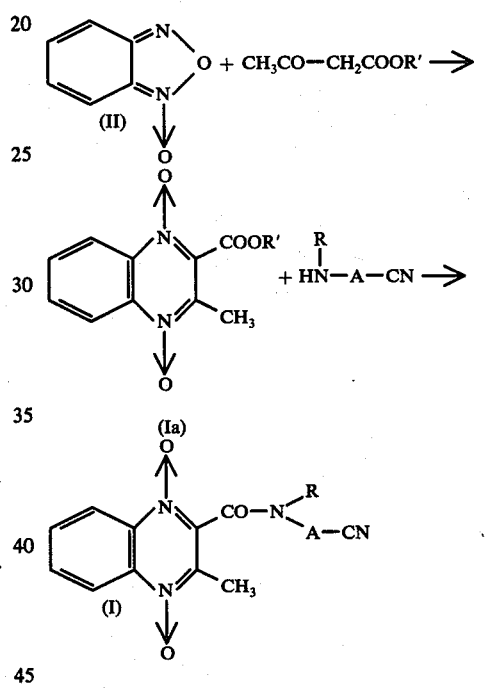

wherein R' represents an alkyl group of 1 to 4 carbon atoms.

The starting materials of the formula III for obtaining the compounds of the present invention of the formula I are partly novel and partly known. They can be obtained by methods which are known per se from amines and diketenes (cf. Houben-Weyl 7/4, page 234 and 8, page 658).

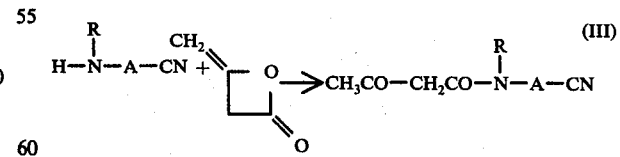

The manufacture of the starting compounds is carried out at temperatures between −15° and +30° C, preferably between −10° and 0° C. The reaction takes place in an organic solvent. Suitable solvents are alcohols, such as ethanol or isopropanol, preferably methanol. It is advantageous to carry out the reaction in anhydrous medium.

The following synthesis is commonly known as a further method of manufacture:

$$CH_3COCH_2COOR' + H\overset{R}{\underset{|}{N}}-A-CN \longrightarrow \qquad (III)$$

$$CH_3COCH_2CO-\overset{R}{\underset{|}{N}}-A-CN$$

The manufacture of the benzofuroxane of the formula III is described in "Organic Syntheses," page 74.

Compounds similar to the compounds of the present invention of the formula I are already known from DOS No. 1,670,935, DOS No. 1,620,114, and from British patent specification No. 1,223,720. The compounds of this invention of the formula I are far superior to the known compounds for controlling pathogenic microorganisms and, compared with them, are characterized in particular by a more pronounced therapeutic action.

The compounds of the formula I have a good microbicidal action and are suitable chiefly for controlling pathogenic microorganisms in the sphere of veterinary medicine. They are characterized especially by an excellent action against diseases of the respiratory tract in poultry caused by E. coli.

Furthermore, the compounds of the formula I of the present invention can be used to combat infections of the intestinal tract, for example swine diarrhoea, and of the urogenital system. In addition, they possess good growth-stimulating properties in domestic animals and productive livestock, such as swine, poultry, and ruminants.

The following compounds are to be singled out for their special activity in respect of their biological properties:

1,4-dioxido-3-methyl-quinoxaline(2)-N-(2'-cyanoethyl)-carboxamide, 1,4-dioxido-3-methyl-quinoxaline(2)-N-(cyanomethyl)-carboxamide, 1,4-dioxido-3-methyl-quinoxaline(2)-N-(1'-cyanoisopropyl)-carboxamide, 1,4-dioxido-3-methyl-quinoxaline(2)-N-(3'-cyanopropyl)-carboxamide, 1,4-dioxido-3-methyl-quinoxaline(2)-N-(4'-cyanobutyl)-carboxamide.

In accordance with the use for which they are intended, the active compounds of the invention can be administered as pure active substance or combined with inert carriers or diluents to the animals direct perorally, abomasally or by injection, in the form of solutions, emulsions, suspensions, powders, tablets, boluses and capsules, both as a single and repeated dose. The active compounds and mixtures containing them can also be added to the feed or drinks or they can be contained in feed premixes.

The surprisingly excellent therapeutic action of the compounds of the formula I of the present invention has been established both in vitro and especially in animals with acute bacterial infections after oral as well as subcutaneous application. The activity spectrum of the compounds encompasses gram-positive and gram-negative bacteria.

As is evident from the following summary of results obtained from comparison tests with known compounds, the superiority of the compounds of the present invention can be unequivocally demonstrated.

In tests carried out on white mice, the intraperitoneally infected animals are treated subcutaneously and perorally as follows:

The administration is effected in doses of 1 mg, 3 mg, 10 mg, 30 mg, 100 mg or 300 mg of active substance per kg of body weight initially simultaneously with the infection and a second time 3 hours later.

Comparison test 1: $\dfrac{ED_{50} \text{ in the mouse septicaemia model}}{(95\% \text{ confidence interval})}$

| Bacteria Compounds | | Staph. aureus Smith | Strept. pyog. Aronson | E. coli 205 | | Salm. ty.-m | | Past. mult. | Pseud. aerug. |
|---|---|---|---|---|---|---|---|---|---|
| | | | | average effective dose/confidence interval in mg of active substance/kg of body weight | | | | | |
| A | 2 × sc. | 10 (7 – 14) | 205 (ED 20) | 3 | (2.2 – 4.2) | 3.9 | (2.6–5.7) | 3.0 (2.1– 4.2) | 120 ( 66– 218) |
|   | 2 × po. | 12 (10 – 15) | 265 (162–433) | 3.5 | (2.5 – 5.0) | 4.2 | (2.9 – 5.7) | 3.4 (2.4 – 4.7) | 75 ( 48–116) |
| B | 2 × sc. | 16 (11 – 22) | 140 (ED 20) | 11 | ( 8 – 15) | 11 | (7.7 – 16) | 3.2 (2.1 – 4.9) | >100 |
|   | 2 × po. | 18 (13 – 24) | 170 (ED 20) | 18 | (13 – 24) | 25 | (17 – 35) | 5.1 (3.6 – 7.1) | >300 |
| C | 2 × sc. | 18 (13 – 24) | 400 (209 – 762) | 5.5 | (4.1 – 7.4) | 10 | (6.5 – 15) | 5.5 (4.0– 7.6) | 105 ( 59 – 186) |
|   | 2 × po. | 27 (19 – 38) | 275 (161 – 468) | 6.6 | (4.8 – 9.1) | 11 | (7.1 – 17) | 3.9 (2.8 – 5.4) | 235 (146 – 378) |
| D | 2 × sc. | 40 (29 – 54) | 425 (296 – 609) | 9 | (6.5– 12.5) | 10 | ( 6 – 17) | 14 (10 – 20) | 210 (140 – 314) |
|   | 2 × po. | 60 (45 – 78) | 410 (297 – 566) | 10 | ( 7 – 13) | 13 | ( 9 – 19) | 15 (10 – 21) | 490 (295 – 814) |
| E | 2 × sc. | 2500 (1425–4375) | — | 300 | (210 – 425) | 140 | ( 95 – 207) | ~100 | — |
|   | 2 × po. | 35 (25 – 50) | — | 30 | (20 – 45) | 25 | (18 – 35) | ~ 30 | — |
| F | 2 × sc. | 200 (150 – 260) | — | 150 | (105 – 215) | ~ 100 | | — | — |
|   | 2 × po. | 280 (210 – 370) | — | 100 | ( 70 – 140) | ~ 100 | | — | — | sc. = subcutaneous
po. = peroral

Comparison test 2: $\dfrac{ED_{50} \text{ in the } E. \text{ coli aerosacculitis model}}{(95\% \text{ confience interval*})}$ Single peroral administration by means of a probang to simultaneously infected hens in mg of active substance per kg of body weight.

| Compounds | $ED_{50}$ | Confidence interval |
|---|---|---|
| A | 2.0 | 1.3 – 3.0 |
| D | 5.3 | 3.7 – 7.6 |
| E | 9.0 | 6.5 – 12.5 |
| F | 11.0 | 8.2 – 14.8 |

A = compound 1
B = compound 2
C = Example 1
D = "Olaquindox" (DOS 1,670,935; compound 6)
E = "Carbadox" (DOS 1,620,114; Example 1)
F = "Grofas" (British patent specification 1,223,720; compound 1, table on page 3).
*J. Pharmacol. Exper. Therap. 96 (1949), 99–113.

DEMONSTRATION OF GROWTH

A group of eight piglets (four ♂ and four ♀) was fed for 28 days with a normal feed containing 17.6% of raw protein and 3.4% of crude fibres and to which 50 ppm of 1,4-dioxido-3-methyl-quinoxaline(2)-N-(2'-cyanoethyl)-carboxamide (Example 1) had been added. The average initial weight of the individual test animals was approx. 9 kg at the start of the test. At the conclusion of the test the animals were weighed individually and the feed consumption determined in groups. For control purposes, a parallel test following the same procedure was carried out using the same feed without the addition of active substance.

Result:

|  | Daily growth rate [1] | | Feed consumption index [1,2] | |
|---|---|---|---|---|
|  | abs. | rel. | abs. | rel. |
| (control) | 231 g | 100% | 1.90 | 100% |
| compound of Example 1 | 305 g | 132% | 1.69 | 88,9% |

[1] Figures in average values
[2] kg of feed consumed per kg of growth in weight.

EXAMPLE 1

1,4-Dioxido-3-methyl-quinoxaline(2)-N-(2'-cyanoethyl)-carboxamide 19.2 g of benzofuroxane are added in small amounts to a solution of 23.8 g of N-2-cyanoethyl-acetoacetic amide in 80 ml of methanol and then ammonia which has been dried over KOH is introduced over the course of 2 hours, while initially keeping the temperature of the solution, which has rapidly turned dark in colour, below 45° C by cooling from time to time. After the formation of the heat of reaction has subsided, the temperature of the reaction mixture is kept at 40°–45° C, and, when the addition of ammonia is complete, the batch is stirred for 10 to 12 hours at the same temperature. The reaction product separates out in beige-colored crystals. After cooling, the crystals are collected with suction and washed with cold methanol. The resultant pure crystalline 1,4-dioxido-3-methyl-quinoxaline(2)-N-(2'-cyanoethyl)-carboxamide melts at 198°–199° C. It can be recrystallized from dimethyl formamide/ethanol.

EXAMPLE 2

1,4-Dioxido-3-methyl-quinoxaline(2)-N-(2'-cyanoethyl)-carboxamide

While stirring at −10° to 0° C, 11.8 g of freshly distilled diketene are added dropwise to a solution of 80 ml of methanol and 9.9 g of aminopropionitrile. The mixture is allowed to warm to room temperature and stirred for a further 2 hours at 35° C. Then 19.2 g of benzofuroxane are added in small amounts to the solution of N-2-cyanoethyl-acetoacetic amide and thereafter ammonia which has been dried over KOH is introduced over the course of 8 hours, while keeping the temperature of the solution, which has rapidly turned dark in color, below 45° C by cooling from time to time. After the formation of the heat of reaction has subsided, the temperature of the reaction mixture is kept at 40°–45° C, and, when the addition of ammonia is complete, the batch is stirred for 10 to 12 hours at the same temperature. The reaction product separates out in the form of beige-colored crystals. After cooling, the crystals are collected with suction and washed with cold methanol. The resultant pure 1,4-dioxido-3-methyl-quinoxaline-(2)-N-(2'-cyanoethyl)-carboxamide melts at 198°–199° C. It can be recrystallized from dimethyl formamide/ethanol.

EXAMPLE 3

Acetoacetic N-cyanomethylamide

While stirring at −10° to 0° C, 92 g of freshly distilled diketene are added dropwise to a solution of 400 ml of methanol and 56 g of freshly distilled aminoacetonitrile. The mixture is allowed to warm to room temperature and stirring is continued for 2 hours at 35° C in a water bath. The solvent is distilled off by rotary evaporation and the solid residue is suspended in cold ether. Suction filtration yields the colourless, crystalline, pure acetoacetic N-cyanomethylamide with a melting point of 63°–65° C.

The following compounds were obtained by a process analogous to that described in Examples 1 and 2:

Compound Table

| Nr. | R | A | Physical data |
|---|---|---|---|
| 1 | H | —$CH_2$— | 214 – 215° C |
| 2 | H | —$\underset{CH_3}{\underset{|}{\overset{CH_3}{\overset{|}{C}}}}$— | 204 – 206° C |
| 3 | $CH_3$ | —$CH_2$—$CH_2$— | 157 – 159° C |
| 4 | H | —$CH_2$—$\underset{CH_3}{\underset{|}{CH}}$— | 175 – 177° C |
| 5 | H | —$\underset{CH_3}{\underset{|}{CH}}$—$CH_2$— | 166 – 168° C |
| 6 | —$CH_2$—$CH_2$—CN | —$CH_2$—$CH_2$— | 206 – 208° C |
| 7 | —$(CH_2)_3$—$CH_3$ | —$CH_2$— | 156 – 157° C |
| 8 | H | —$(CH_2)_3$— | 157 – 159° C |
| 9 | H | —$(CH_2)_4$— | 166 – 168° C |
| 10 | H | —$\underset{CH_2-CH_3}{\underset{|}{CH}}$— | 223 – 224° C |
| 11 | —$(CH_2)_3$—$CH_3$ | —$CH_2$—$CH_2$— |  |
| 12 | —$(CH_2)_{11}$—$CH_3$ | —$CH_2$—$CH_2$— | $n_D^{28}$ 1.558 |
| 13 | —$CH_2$—CH=$CH_2$ | —$CH_2$—$CH_2$— |  |
| 14 | H | —$\underset{CH_3}{\underset{|}{CH}}$— | 197 – 198° C |
| 15 | —$(CH_2)_5$—$CH_3$ | —$CH_2$—$CH_2$— | $n_D^{28}$ 1.566 |

EXAMPLE 4

Feed Additives

The following feed mixes were prepared to obtain individual amounts of 6000 parts by weight of end feed containing (a) 25 ppm, (b) 50 ppm, (c) 200 ppm and (c) 400 ppm:

(a)

0.15 part by weight of one of the compounds of the formula I
49.85 parts by weight of *Bolus alba*
150.0 parts by weight of standard feed for poultry, swine or ruminants.

(b)

0.03 part by weight of one of the compounds of formula I
44.70 parts by weight of *Bolus alba*
5.0 parts by weight of silicic acid
150.0 parts by weight of standard feed for poultry, swine or ruminants.

(c)

1.2 parts by weight of one of the compounds of the formula I
43.8 parts by weight of *Bolus alba*
5.0 parts by weight of silicic acid
150.0 parts by weight of standard feed for poultry, swine and ruminants.

(d)

2.4 parts by weight of one of the compounds of formula I
47.6 parts by weight of *Bolus alba*
150.0 parts by weight of standard feed for poultry, swine or ruminants.

The active substances are mixed with the carrier materials either direct or applied thereto dissolved in chloroform, and the mixtures are subsequently ground to the desired particle size of, for example, 5 to 10 μ. The feed premixes are mixed with 5800 parts by weight of standard feed or processed to 6000 parts by weight of ready-for-use beverages. In addition, the end feed mixes can be processed to pellets (feed pellets).

The active compounds of the formula I are added to the feed or beverages for the animals in amounts of 1 to 500 ppm, referred to the total feed or beverage, either direct or in the form of a premix.

Suitable premixes consist for example of a mixture of the active compound with kaolin, chalk, alumina, ground mussel shells, *Bolus alba*, aerosol, starch or lactose. A feed mix is prepared by thoroughly mixing the required amount of premix with the corresponding amount of a standard commercial feed.

We claim:

1. Quinoxaline-di-N-oxide derivatives of the formula I

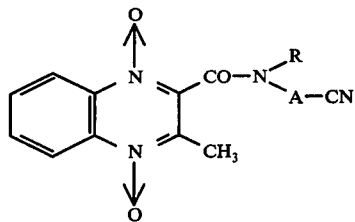

wherein
R represents a hydrogen atom, an alkyl group of 1 to 12 carbon atoms, a cyanoalkyl group having 1 to 4 carbon atoms in the alkyl moiety or an allyl group, and
A represents a straight-chain or branched alkylene bridge member containing 1 to 4 carbon atoms.

2. A compound as claimed in claim 1 which is 1,4-Dioxido-3-methyl-quinoxaline(2)-N-(2'-cyanoethyl)-carboxamide.

3. A compound as claimed in claim 1 which is 1,4-Dioxido-3-methyl-quinoxaline(2)-N-(cyanomethyl)-carboxamide.

4. A compound as claimed in claim 1 which is 1,4-Dioxido-3-methyl-quinoxaline(2)-N-(1'-cyanoisopropyl)-carboxamide.

5. A compound as claimed in claim 1 which is 1,4-Dioxido-3-methyl-quinoxaline(2)-N-(3'-cyanopropyl)-carboxamide.

6. A compound as claimed in claim 1 which is 1,4-Dioxido-3-methyl-quinoxaline(2)-N-(4'-cyanobutyl)-carboxamide.

7. A composition for controlling pathogenic microorganisms, which contains as active component an effective amount of at least one compound of the formula I according to claim 1, together with an inert carrier therefor.

8. A composition for combating diseases of the respiratory tract in poultry caused by *E. coli*, which contains as active component an effective amount of at least one compound of the formula I according to claim 1, together with an inert carrier therefor.

9. A composition for stimulating the growth of domestic animals and productive livestock, which contains as active component an effective growth stimulating amount of at least one compound of the formula I according to claim 1, together with an inert carrier therefor.

10. A method of combatting pathogenic microorganisms, which comprises administering to the host afflicted with said microorganisms an effective amount of a compound of the formula I according to claim 1.

11. A method of combatting diseases of the respiratory tract in poultry caused by *E. coli* which comprises administering to said poultry an effective amount of a compound of the formula I according to claim 1.

12. A method of promoting the growth of domestic animals and productive livestock, which comprises administering to said animals and livestock an effective growth promoting amount of a compound of the formula I according to claim 1.

* * * * *